(12) United States Patent
Loescher et al.

(10) Patent No.: US 7,615,673 B2
(45) Date of Patent: Nov. 10, 2009

(54) PROPYLENE OLIGOMERIZATION PROCESS

(75) Inventors: Mitchell E. Loescher, Houston, TX (US); Christopher C. Boyer, Houston, TX (US); Michael J. Keenan, Baton Rouge, LA (US); Jon E. R. Stanat, Baton Rouge, LA (US)

(73) Assignees: Catalytic Distillation Technologies, Pasadena, TX (US); ExxonMobil Chemical Patents Inc., Baytown, TX (US)

( * ) Notice: Subject to any disclaimer, the term of this patent is extended or adjusted under 35 U.S.C. 154(b) by 293 days.

(21) Appl. No.: 11/518,372

(22) Filed: Sep. 8, 2006

(65) Prior Publication Data
US 2008/0064911 A1 Mar. 13, 2008

(51) Int. Cl.
C07C 2/02 (2006.01)
(52) U.S. Cl. .................. 585/533; 585/520; 585/530; 585/532
(58) Field of Classification Search .......... 585/502, 585/520, 510, 530, 532, 533
See application file for complete search history.

(56) References Cited

U.S. PATENT DOCUMENTS

| 4,215,011 | A | 7/1980 | Smith, Jr. |
|---|---|---|---|
| 4,870,038 | A | 9/1989 | Page et al. |
| 4,956,514 | A | 9/1990 | Chu |
| 5,149,896 | A | 9/1992 | Bellussi et al. |
| 6,072,093 | A | 6/2000 | O'Neill et al. |
| 6,143,942 | A | 11/2000 | Verrelst et al. |
| 2002/0111523 | A1 | 8/2002 | Mathys et al. |
| 2005/0049448 | A1* | 3/2005 | Loescher et al. ............ 585/533 |
| 2007/0123743 | A1* | 5/2007 | Ng et al. .................... 585/260 |

FOREIGN PATENT DOCUMENTS

WO 9522516 8/1995

OTHER PUBLICATIONS

Notification of Transmittal of the International Search Report and the Written Opinion of the International Searching Authority, or the Declaration Dated Feb. 1, 2008 pp. 11.

* cited by examiner

*Primary Examiner*—In Suk Bullock
(74) *Attorney, Agent, or Firm*—Osha • Liang LLP (57) ABSTRACT

A process for the oligomerization of propylene is disclosed wherein MCM-22 zeolite prepared as a distillation structure is used in a reaction distillation zone under conditions of temperature and pressure to concurrently react the propylene to produce oligomers thereof and separate the oligomer products from unreacted propylene by fractional distillation in a distillation column reactor. Compared to the prior art tubular or plug flow reactors, lower temperatures and pressures are used to produce higher conversions and selectivities to preferred isomeric forms.

18 Claims, 2 Drawing Sheets

PROPYLENE OLIGOMERIZATION PROCESS

BACKGROUND OF THE INVENTION

1. Field of the Invention

The present invention relates to a process for converting propylene over MCM-22 zeolite catalyst to provide higher molecular weight hydrocarbons, particularly $C_6$, $C_9$ and $C_{12}$ olefins. More particularly the conversion is carried out simultaneously with distillation in a distillation column reactor.

2. Related Information

In the present state of the art the catalysts are used in tubular reactors at severe conditions, i.e., 330-482° F. and 1000 to 1215 psig pressures. Prior catalysts which have been used for the oligomerization of propylene include supported phosphoric acid (sPa), metal complexes (U.S. Pat. Nos. 5,510,555; 4,695,664 and 6,501,001) and various zeolites, especially ZSM-22 and ZSM-57 (U.S. Pat. No. 6,143,942). These reaction systems have undesirable qualities characterized as one or more of: severe reaction conditions, short catalyst life and poor selectivity.

The reaction requires high temperature (330-482° F.) and high pressure (1000 to 1215 psig). The sPa system has a life of less than 1000 tons of product per ton of catalyst and then must be removed and discarded. The zeolites have shown increased life, e.g., 1500 to 3000 tons of product per ton of catalyst, but lose activity and must be regenerated at considerable expense. U.S. Pat. No. 6,072,093 teaches that the catalyst life may be extended by recycling cycloparaffins through the tubular reactor, which requires additional separation and recycling apparatus and an inventory of the non associated cycloparaffins. The metal complexes are homogeneous catalysts wherein the catalyst and the products must be separated with continuous catalyst makeup required. The selectivity of the sPa is toward the $C_9$ and heavier while the preferred oligomers are the $C_6$ and $C_9$ which are converted to alcohols. The selectivities of the zeolites and metal complexes are somewhat better.

U.S. Pat. No. 4,956,514 discloses zeolite MCM-22 which has been shown to have favorable characteristics for the oligomerization of propylene at lower pressures and temperatures than the other catalyst.

U.S. Pat. No. 4,242,430 discloses the dimerization of isobutylene in a distillation column reactor using an acidic cation exchange resin as the catalyst which avoided the formation of higher oligomers.

SUMMARY OF THE INVENTION

Briefly the present invention is a process for the oligomerization of propylene comprising: contacting propylene with MCM-22 zeolite catalyst in a reaction distillation zone under conditions of temperature and pressure to concurrently react the propylene to produce oligomers thereof and separate the oligomer products from unreacted propylene by fractional distillation.

It has been found that the oligomerization of propylene over MCM-22 zeolite in a distillation column reactor may be carried out at lower temperatures, below 300° F. preferably less than 200° F., and pressures, below about 500 psig, than in the prior art tubular reactors to produce a higher conversion to more desirable oligomeric isomer forms. The conditions for the present reaction are much less severe than that required by earlier zeolite oligomerization processes including those using MCM-22 zeolite. The distillation column reactor preferably operates at a pressure in the range of 200-450 psig and temperatures in the range of about 140 to 200° F., preferably 158° to 185° F. Conversions of about 70 to 75% have been achieved yielding about 20% hexene and 55% nonene. The branched type of product is particularly suited for oxy chemistry.

As used herein the term "distillation column reactor" means a distillation column which also contains catalyst such that reaction and distillation are going on concurrently in the column. In a preferred embodiment the zeolite MCM-22 catalyst is prepared as a distillation structure and serves as both the catalyst support and distillation structure.

DESCRIPTION OF THE PREFERRED EMBODIMENT

The normal feed for the oligomerization is a $C_3$ cut, which contains 20 to 100 mole % propylene. The balance is predominately propane, with minor amounts of ethylene, ethane and the lighter $C_4$'s.

The column may be operated in up flow mode or down flow mode. In up flow mode, the feed (propane and propylene) is placed below the catalyst bed. The reactants are boiled up into the catalyst where they react and the heavier oligomer product is removed out the bottom of the distillation column reactor. Unreacted propylene and inert propane are removed for the top of the distillation column reactor and may be recycled back into the reactor after adjusting for the propane/propylene content.

In down flow mode the column is operated such that the feed (propane and propylene) enters the top of the column, while oligomer product and inert propane are removed from the bottom of the distillation column reactor. The reactive component, propylene, is the lighter component and becomes concentrated in the top of the column by distillation. The catalyst bed is placed in the top of the column where the propylene concentration bulges. Overhead distillate flow may be minimized such that the propylene is refluxed to exhaustion.

Catalyst life is improved when using the MCM-22 as packing in a distillation column reactor. The unique hydraulic action in a distillation column washes out the heavy oligomers as they are produced and prevents fouling. Zeolite MCM-22 is described in detail in U.S. Pat. No. 4,956,514 which is incorporated herein.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and /or germanium, preferably silicon, and n is at least about 10, usually from about 10 to about 150, more usually form a bout 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005\text{-}0.1)Na_2O_2:(1\text{-}4)R:X_2O_3:nYO_2$$

wherein R is an organic component. The Na and R components are associated with the zeolite as a result of their presence during crystallization, and are easily removed by post-crystallization methods known in the art such as ion exchange.

Zeolite MCM-22 is thermally stable and exhibits high surface area greater than 400 m²/gm as measured by the BET test and unusually large sorption capacity when compared to previously described crystal structures having similar X-ray diffraction patterns. As is evident from the above formula, MCM-22 is synthesized nearly free of Na cations. It can, therefore, be used as an olefin oligomerization catalyst wit acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the activity of the catalyst for olefin oligomerization. These include hydrogen, rare earth metals and metals of Groups IIA, IIIA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing(Å) | Relative Intensity, I/Io × 100 |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More particularly, the calcined form may be characterized by and X-ray diffraction pattern including the following lines:

TABLE II

| Interplanar d-Spacing(Å) | Relative Intensity, I/Io × 100 |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |

TABLE II-continued

| Interplanar d-Spacing(Å) | Relative Intensity, I/Io × 100 |
| --- | --- |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values are determined by standard techniques. The radiation was the K-alpha doublet of copper and diffractometer equipped with a scintillation counter and an associated computer is used. The peak heights, I, and the positions as a function of 2 theta, where theta is the Bragg angle, are determined using algorithms on the computer associated with the diffractometer. From these, the relative intensities, 100 I/$I_o$, where $I_o$ is the intensity of the strongest line or peak, and d(obs.) the interplanar spacing in Angstroms Units (Å), corresponding to the recorded lines, are determined. In Tables I and II the relative intensities are given in terms of symbols W=weak, M=medium, S=strong, and VS=very strong. In terms of intensities these may be generally designated as follows:

W=0-20
M=20-40
S=40-60
VS=60-100

It should be understood that these X-ray diffraction patterns are characteristic of all species of the present MCM-22 crystalline composition. The sodium form as well as other cationic forms reveal substantially the same pattern with some minor shifts interplanar spacing and variation in relative intensity. Other minor variations can occur depending on the Y to X, e.g. silicon to aluminum, mole ratio of the particular sample as well as its degree of thermal treatment.

Prior to its use as an olefin oligomerization catalyst, the MCM-22 crystals should be subjected to thermal treatment to remove part or all of any organic constituents present therein. In addition the zeolite MCM-22 crystals should be dehydrated, at least partially. This can be done by heating the crystals to a temperature in the range of form abut 200 C, to about 595 C in an inert atmosphere, such as air, nitrogen and the like and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolites, including MCM-22, as provided are much too fine to function as catalytic distillation structures in a distillation column reactor as required by the present invention. The catalytic distillation structure must be able to function as catalyst and as mass transfer medium. The catalyst is preferably supported and spaced within the column to act as a catalytic distillation structure. The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structures. Catalytic distillation structures useful for this purpose are disclosed in U.S. Pat. Nos. 4,731,229, 5,073,236, 5,431,890, 5,266,546 and 5,730,843 which are incorporated by reference. A preferred catalytic distillation structure embodiment is described in U.S. Pat. No. 5,431,890.

Figure 1:
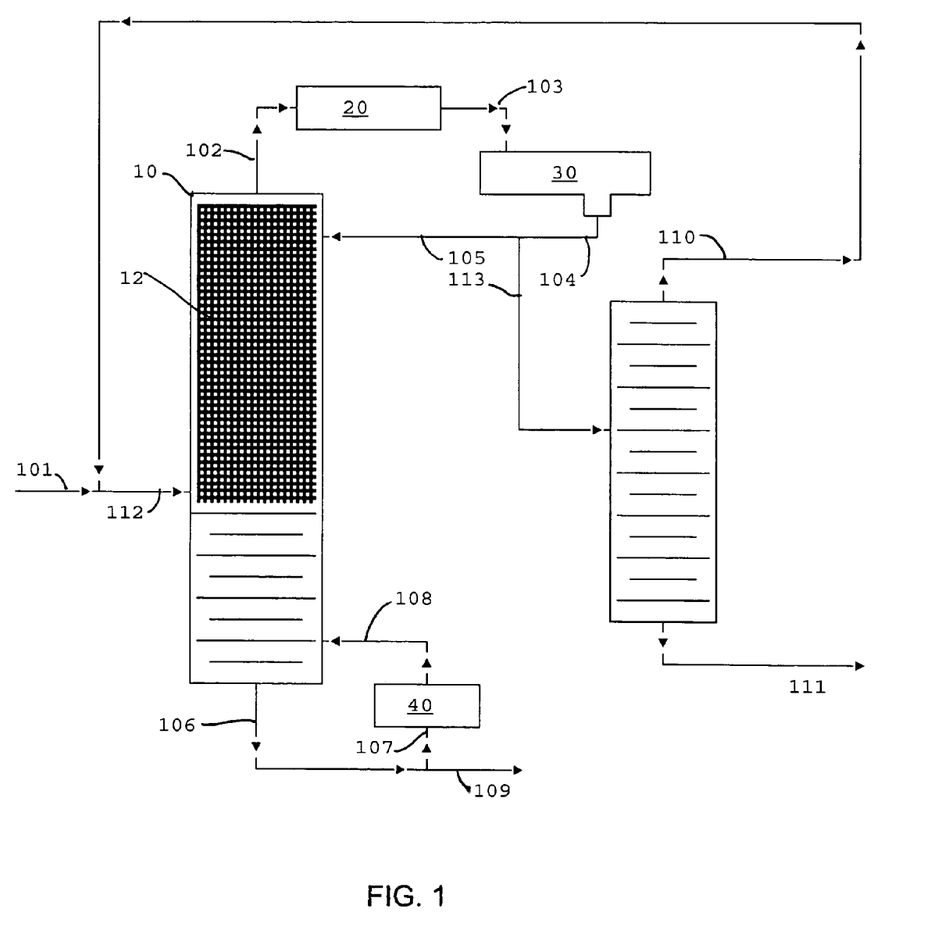
FIG. 1 is a simplified flow diagram of the invention with the distillation column reactor operated in the up flow mode.

Referring now to FIG. 1 the operation of the distillation column reactor in the up flow mode is shown. Fresh feed which includes propylene in via flow line 101 is combined with recycle from flow line 110 in flow line 112 and fed to distillation column reactor 10 below a bed 12 of MCM-22 zeolite catalyst prepared as a distillation structure. The reactants are boiled up into the bed where the propylene reacts with itself and dimers of itself to produce the oligomer products, mainly $C_6$, $C_9$ and $C_{12}$ oligomers. The oligomer products, being higher boiling, are removed from the distillation column reactor as bottoms via flow line 109. A portion of the bottoms are cycled through reboiler 40 via flow lines 107 and 108. Unreacted propylene and inert propane are removed from the distillation column reactor 10 as overheads via flow line 102, condensed in condenser 20 and collected in receiver 30. The condensed liquid is removed from the receiver 30 via flow line 104 with a portion being returned to distillation column 10 as reflux. The remainder of the liquid distillate is passed to distillation column 50 where the propane is separated from the mixture and removed as bottoms via flow line 111. The propylene, along with some propane, is taken as overheads via is recycled to distillation column reactor 10 via flow line 110.

Figure 2:
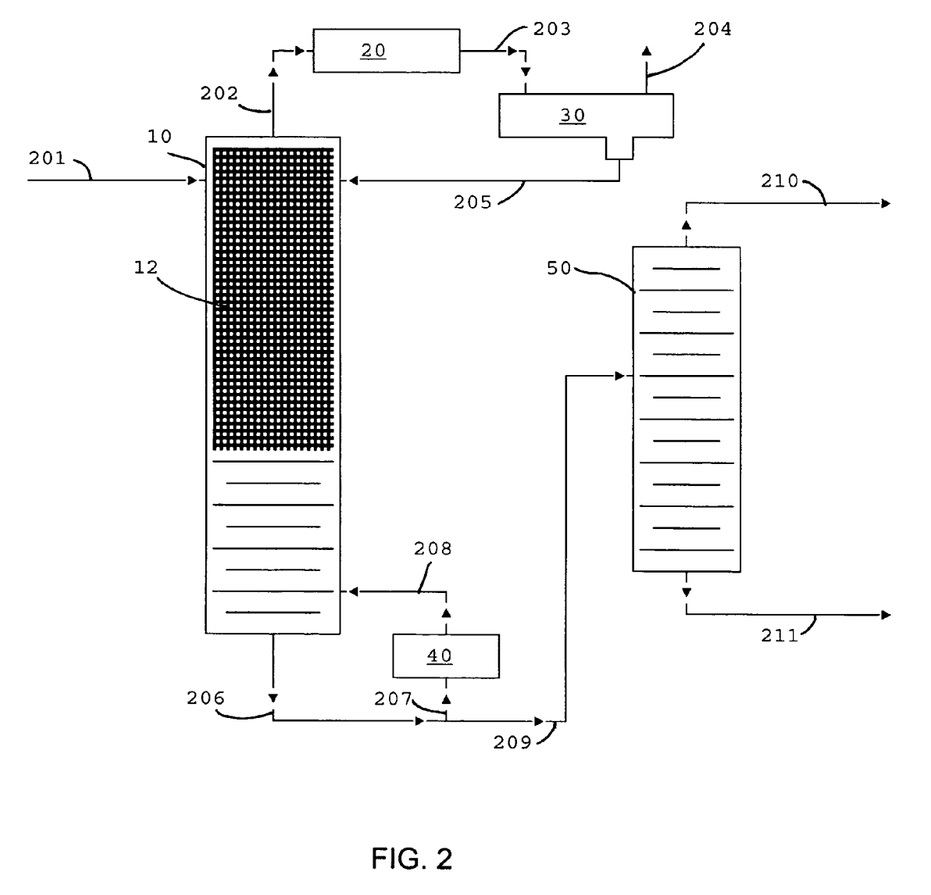
FIG. 2 is a simplified flow diagram of the invention with the distillation column reactor operated in the down flow mode.

Referring now to FIG. 2 the operation of the distillation column reactor in the down flow mode is shown. Feed containing propylene in flow line 201 is fed to the top of the distillation column 10 having a bed 12 of the MCM-22 zeolite catalyst as distillation structure. The reactive propylene is the lighter component and is concentrated in the upper part of the column containing the MCM-22 zeolite. Some unreacted propylene is taken as overheads via flow line 202, condensed in condenser 20 and thence to receiver 30 via flow line 203 where all of the liquid is returned as reflux to the column 10 via flow line 205 assuring essentially complete conversion. A purge via flow line 204 is provided to prevent build up. The propylene reacts with itself and dimers of itself in the catalyst bed 12 to produce the desired oligomer product, mostly C6, C9 and C12 oligomers. The oligomer product and inert propane are removed as bottoms from the distillation column reactor 10 via flow line 206 and fed to distillation column 50 via flow line 209 where the propane is separated as overheads via flow line 210 from the oligomer product which is taken as bottoms via flow line 211.

As used herein the description "feeding at the top of the bed" includes feed above the catalyst bed and the description "feeding at the bottom of the bed" includes feed below the catalyst bed.

TABLE III below presents comparative data showing results using various processes including the present invention. In the MODE section CD=catalytic distillation or the use of a catalytic distillation column.

TABLE III

| Catalyst | sPa | ZSM-22 | ZSM-27 | MCM-22 | MCM-22 |
|---|---|---|---|---|---|
| Reactor Mode | tubular | tubular | tubular | CD | CD |
| Propylene feed* | | | | Down flow | Up flow |
| Temp., ° F. | 330-482 | 330-482 | 330-482 | 158-165 | 166-172 |
| Pressure, psig | 1000-1215 | 1000-1215 | 1000-1215 | 400 | 400 |
| Cat. Life (Ton/Ton) | <1000 | 1500-2000 | 2000-3000 | TBD | TBD |
| Conv. Wt % | NA | NA | NA | 70-75 | 70 |
| Selectivity | | | | | |
| $C_6=$ | 4 | 36 | 3.5 | 20.1 | 20 |
| $C_7=$ | 5 | $\leqq 1$ | 2 | 3.0 | — |
| $C_8=$ | 9 | $\leqq 1$ | 2.5 | 0.0 | — |
| $C_9=$ | 52 | 36 | 71 | 54.8 | 50 |
| $C_{10}\text{-}C_{11}=$ | 10 | 1.5 | 1.5 | 3.1 | — |
| $C_{12}=$ | 15 | 17 | 13 | 12.0 | 28 |
| $C_{12}+=$ | 4 | 6 | 6 | 7.0 | <2 |

*Down flow = fed at the top o the catalyst bed, Up flow = fed at the bottom of the catalyst bed The product selectivity can be affected independently of the conversion by adjusting the number of catalytic distillation stages in the distillation column reactor. Increasing the number of stages containing the MCM-22 catalyst produces more of the heavier product. The conversion is affected by the reflux rate to feed rate.

In the Hexene product the MCM-22 catalyst produced more Type I and Type II branching than the other types of catalyst. See TABLE IV below. The Type I branching is particularly suited for oxy chemistry, which is a primary use of oligomer olefins.

TABLE IV

| | Catalyst | | | |
|---|---|---|---|---|
| Branching type (Hexenes) | sPa | ZSM-22 tubular | ZSM-57 | MCM-22 CD |
| Type I | 1.3 | 2.4 | NA | 66.6 |
| Type II | 19.4 | 17.6 | NA | 24.0 |
| Type III | 6.7 | 10.1 | NA | 0.8 |
| Type IV | 39.4 | 61.2 | NA | 7.0 |
| Type V | 5.6 | 0.6 | Na | 0.0 |

In the nonene product the MCM-22 catalyst produced more Type I and substantially as much Type II branching as the other commonly used catalysts. See TABLE V below.

TABLE V

| Branching type (Nonenes) | Catalyst | | | |
|---|---|---|---|---|
| | sPa | ZSM-22 tubular | ZSM-57 | MCM-22 CD |
| Type I | 1.7 | 2.0 | 1.0 | 31.4 |
| Type II | 14.2 | 19.8 | 13.9 | 16.7 |
| Type III | 8.2 | 7.6 | 7.2 | 4.5 |
| Type IV | 64.2 | 61.1 | 56.7 | 30.7 |
| Type V | 11.8 | 10.4 | 21.2 | 16.6 |

The invention claimed is:

1. A process for the oligomerization of propylene comprising:
   contacting propylene with MCM-22 zeolite catalyst prepared as a distillation structure in a reaction distillation zone under conditions of temperature and pressure to concurrently:
      react the propylene to produce oligomers thereof; and
      separate the oligomer products from unreacted propylene by fractional distillation;
   wherein a conversion of propylene is at least 70 wt. %;
   wherein a selectivity to $C_6$ and $C_9$ oligomers is at least 70%; and
   wherein the $C_6$ and $C_9$ oligomers consist of an isomeric mixture having at least 90% type I and type II branching.

2. A process for the oligomerization of propylene comprising the steps of:
   (a) feeding a stream containing propylene to a distillation column reactor containing a bed of MCM-22 zeolite catalyst; and
   (b) concurrently in said distillation column reactor at a pressure below about 500 psig;
      (i) reacting the propylene to produce oligomers, and
      (ii) separating the oligomer products from unreacted propylene by fractional distillation;
   wherein a conversion of propylene is at least 70 wt. %;
   wherein a selectivity to $C_6$ and $C_9$ oligomers is at least 70%; and
   wherein the $C_6$ and $C_9$ oligomers consist of an isomeric mixture having at least 90% type I and type II branching.

3. The process according to claim 2 wherein said bed of MCM-22 zeolite catalyst is contained within the upper half of said distillation column reactor.

4. The process according to claim 3 wherein said stream containing propylene is fed to the top of said bed of MCM-22 zeolite catalyst.

5. The process according to claim 4 wherein said overheads is condensed and substantially all of said overheads is returned to said distillation column reactor as reflux.

6. The process according to claim 3 wherein said stream containing propylene is fed at the bottom of said bed of MCM-22 zeolite catalyst.

7. The process according to claim 3 wherein said stream containing propylene also contains propane.

8. The process according to claim 7 wherein said stream containing propylene is fed above said bed of MCM-22 zeolite catalyst.

9. The process according to claim 8 wherein propane is removed in said bottoms along with oligomer products and said bottoms is fed to a distillation column where said propane is separated from said oligomer products.

10. The process according to claim 7 wherein said stream containing propylene is fed below said bed of MCM-22 zeolite catalyst.

11. The process according to claim 10 wherein propane is removed in said overheads along with unreacted propylene and said overheads are fed to a distillation column where propane is separated from propylene.

12. The process according to claim 2, further comprising:
   (c) withdrawing oligomer products from said distillation column reactor as bottoms; and
   (d) withdrawing unreacted propylene from said distillation column reactor as overheads.

13. The process according to claim 12 wherein:
   said stream contains propylene and propane, and is fed to said distillation column reactor at a point above said bed;
   said oligomer products and propane are removed from said distillation column reactor as bottoms, the process further comprising:
   (e) condensing said overheads and returning substantially all of said condensed overheads to said distillation column reactor as reflux; and
   (f) feeding said bottoms to a distillation column where oligomer products are separated as a second bottoms from propane as a second overheads.

14. The process according to claim 12 wherein:
   said stream contains propylene and propane, and is fed to said distillation column reactor at a point below said bed;
   said overheads contains unreacted propylene and propane, the process further comprising:
   (e) condensing said overheads and returning a portion of said condensed overheads to said distillation column reactor as reflux;
   (f) feeding the remainder of said overheads to a distillation column where propane is separated as a second bottoms from propylene as a second overheads; and
   (g) returning said second overheads to said distillation column reactor as feed.

15. The process according to claim 8 wherein the temperature within said bed is between 158-165° F. and the overhead pressure of said distillation column reactor is in the range of 200-450 psig.

16. The process according to claim 10 wherein the temperature within said bed is between 166-172° F. and the overhead pressure of said distillation column reactor is in the range of 200-450 psig.

17. The process according to claim 1, wherein the $C_6$ oligomers consist of an isomeric mixture having at least 90% type I and type II branching.

18. The process according to claim 2, wherein the $C_6$ oligomers consist of an isomeric mixture having at least 90% type I and type II branching.

* * * * *

UNITED STATES PATENT AND TRADEMARK OFFICE
CERTIFICATE OF CORRECTION

| | |
|---|---|
| PATENT NO. | : 7,615,673 B2 |
| APPLICATION NO. | : 11/518372 |
| DATED | : November 10, 2009 |
| INVENTOR(S) | : Mitchell E. Loescher et al. |

It is certified that error appears in the above-identified patent and that said Letters Patent is hereby corrected as shown below:

In the Claims:

Col. 7, claim 1 line 27, and 2, line 43, it reads "90%" and should read -- 48% --.

Col. 7, claim 5, line 1, it reads "wherein said overheads is condensed" and should read --wherein said <u>unreacted propylene is recovered as an overheads from said distillation column reactor</u>, said overheads is condensed --.

Col. 8, claim 9, line 1, it reads "wherein propane is removed in said bottoms along with oligomer products" and should read --wherein propane is <u>recovered as a bottoms from said distillation column reactor</u> along with oligomer products --.

Col. 8, claim 11, line 1, it reads "wherein propane is removed in said overheads along with unreacted propylene" and should read -- wherein propane is <u>recovered as an overheads from said distillation column reactor</u> along with unreacted propylene --.

Col. 8, claim 15, line 1, it reads "wherein the temperature within said bed is between 158-165° F. and the overhead pressure" and should read -- wherein <u>said bed is at a temperature</u> between 158-65° F. and <u>an</u> overhead pressure --.

UNITED STATES PATENT AND TRADEMARK OFFICE
CERTIFICATE OF CORRECTION

PATENT NO.        : 7,615,673 B2
APPLICATION NO.   : 11/518372
DATED             : November 10, 2009
INVENTOR(S)       : Mitchell E. Loescher et al.

It is certified that error appears in the above-identified patent and that said Letters Patent is hereby corrected as shown below:

Col. 8, claim 16, line 1, it reads "wherein the temperature within said bed is between 166-172° F. and the overhead pressure" and should read -- wherein <u>said bed is at a temperature</u> between 166-172° F. and <u>an</u> overhead pressure --.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,615,673 B2
APPLICATION NO. : 11/518372
DATED : November 10, 2009
INVENTOR(S) : Mitchell E. Loescher et al.

It is certified that error appears in the above-identified patent and that said Letters Patent is hereby corrected as shown below:

In the Claims:

Col. 7, claim 1 line 27, and 2, line 43, it reads "90%" and should read -- 48% --.

Col. 7, claim 5, line 55, it reads "wherein said overheads is condensed" and should read -- wherein said <u>unreacted propylene is recovered as an overheads from said distillation column reactor</u>, said overheads is condensed --.

Col. 8, claim 9, line 1, it reads "wherein propane is removed in said bottoms along with oligomer products" and should read -- wherein propane is <u>recovered as a bottoms from said distillation column reactor</u> along with oligomer products --.

Col. 8, claim 11, line 8, it reads "wherein propane is removed in said overheads along with unreacted propylene" and should read -- wherein propane is <u>recovered as an overheads from said distillation column reactor</u> along with unreacted propylene --.

Col. 8, claim 15, line 44, it reads "wherein the temperature within said bed is between 158-165° F. and the overhead pressure" and should read -- wherein <u>said bed is at a temperature</u> between 158-65° F. and <u>an</u> overhead pressure --.

CERTIFICATE OF CORRECTION (continued)
U.S. Pat. No. 7,615,673 B2

Col. 8, claim 16, line 48, it reads "wherein the temperature within said bed is between 166-172° F. and the overhead pressure" and should read -- wherein <u>said bed is at a temperature</u> between 166-172° F. and <u>an</u> overhead pressure --.

This certificate supersedes the Certificate of Correction issued December 29, 2009.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,615,673 B2 | Page 1 of 1 |
| APPLICATION NO. | : 11/518372 | |
| DATED | : November 10, 2009 | |
| INVENTOR(S) | : Loescher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 356 days.

Signed and Sealed this

Nineteenth Day of October, 2010

David J. Kappos
*Director of the United States Patent and Trademark Office*